United States Patent [19]
Pall et al.

[11] Patent Number: 5,266,219
[45] Date of Patent: Nov. 30, 1993

[54] DEVICE AND METHOD FOR SEPARATING PLASMA FROM BLOOD

[75] Inventors: David B. Pall, Roslyn Estates; Thomas C. Gsell; Vlado I. Matkovich, both of Glen Cove; Harvey Brandwein, East Hills, all of N.Y.

[73] Assignee: Pall Corporation, Glen Cove, N.Y.

[21] Appl. No.: 745,166

[22] Filed: Aug. 15, 1991

Related U.S. Application Data

[63] Continuation-in-part of Ser. No. 458,409, Dec. 28, 1989, abandoned.

[51] Int. Cl.$^5$ ............................................ B01D 37/00
[52] U.S. Cl. ...................... 210/767; 210/488; 210/491; 210/508; 422/56; 422/57; 422/60; 422/61; 436/160; 436/170; 436/177
[58] Field of Search ............... 210/645, 649, 650, 651, 210/767, 806, 321.84, 321.85, 435, 237, 436, 500.38, 446, 500.21, 488, 489, 490, 491, 492, 496, 505, 508, 509; 604/406; 422/101, 102, 56, 57, 60, 61, 70; 436/8, 63, 169, 170, 177, 178

[56] References Cited

U.S. PATENT DOCUMENTS

| | | | |
|---|---|---|---|
| 3,877,978 | 4/1975 | Kremen et al. | 210/508 |
| 4,443,492 | 4/1984 | Roller | 427/44 |
| 4,459,210 | 7/1984 | Murakami et al. | 428/398 |
| 4,477,575 | 10/1984 | Vogel et al. | 436/170 |
| 4,617,124 | 10/1986 | Pall et al. | 210/638 |
| 4,620,932 | 11/1986 | Howery | 210/808 |
| 4,702,947 | 10/1987 | Pall et al. | 210/508 |
| 4,786,603 | 11/1988 | Wielinger et al. | 436/69 |
| 4,816,224 | 3/1989 | Vogel et al. | 422/55 |
| 4,833,087 | 5/1989 | Hinckley | 435/287 |
| 4,880,548 | 11/1989 | Pall et al. | 210/767 |
| 4,883,764 | 11/1989 | Kloepfer | 436/63 |
| 4,925,572 | 5/1990 | Pall | 210/767 |
| 4,933,092 | 6/1990 | Aunet et al. | 210/729 |
| 4,936,998 | 6/1990 | Nishimura et al. | 210/767 |
| 4,985,153 | 1/1991 | Kuroda et al. | 210/496 |
| 4,987,085 | 1/1991 | Allen et al. | 436/169 |
| 5,019,260 | 5/1991 | Gsell et al. | 210/490 |
| 5,100,564 | 3/1992 | Pall et al. | 210/514 |

FOREIGN PATENT DOCUMENTS

| | | |
|---|---|---|
| 0267286 | 5/1988 | European Pat. Off. |
| 0370584 | 5/1990 | European Pat. Off. |
| 0397403 | 11/1990 | European Pat. Off. |
| 2511872 | 3/1983 | France |

*Primary Examiner*—Robert A. Dawson
*Assistant Examiner*—Sun Uk Kim
*Attorney, Agent, or Firm*—Leydig, Voit & Mayer

[57] ABSTRACT

A device for separating plasma from blood is provided comprising a synthetic polymeric fibrous structure having a CWST in excess of 65 dynes/cm, the structure having a first region for receiving a blood sample and a second region for accumulating plasma.

51 Claims, 3 Drawing Sheets

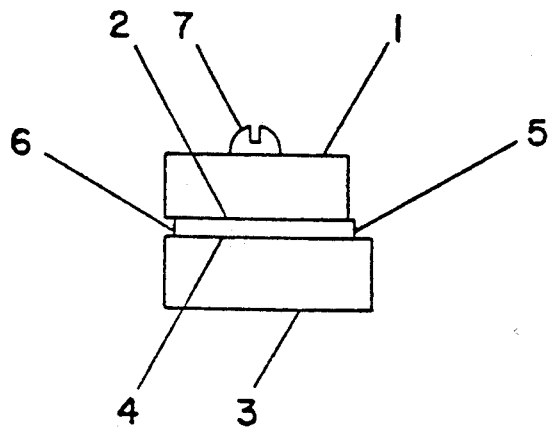
FIG. 1
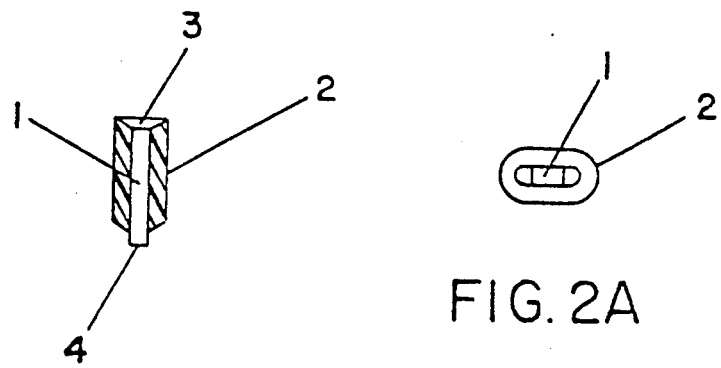
FIG. 2
FIG. 2A
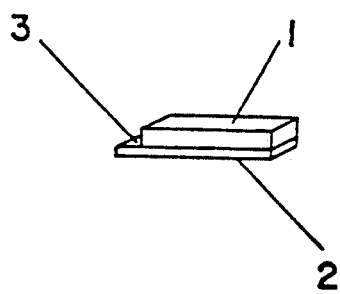
FIG. 3
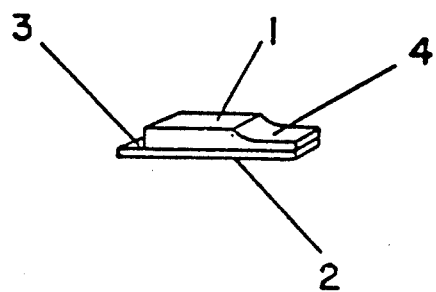
FIG. 4

DEVICE AND METHOD FOR SEPARATING PLASMA FROM BLOOD

RELATED APPLICATIONS

This is a continuation-in-part copending application Ser. No. 458,409, filed Dec. 28, 1989, now abandoned.

TECHNICAL FIELD

This invention relates to devices and methods for separation of components of complex suspensions and, more particularly, of cellular fluids such as blood and, particularly, the separation of plasma from whole blood. The devices and methods of the invention permits efficient and selective separation of blood components, and are particularly useful as diagnostic devices or components thereof.

BACKGROUND OF THE INVENTION

A large number and variety of tests for different diagnostic purposes directed to body fluids such as saliva, urine, blood, cerebrospinal fluid, ascites, etc., have been developed. This invention is directed primarily to diagnostic tests applied to blood, which may for example be obtained from a drop or two squeezed from a finger prick, or may be blood drawn into an anti-coagulant for test purposes or for transfusion, or any other blood product in which red cells are suspended in plasma or in saline, or in other fluid compatible with red cells. Many of these tests rely on colorimetric or spectrophotometric evaluation of a reaction of a fluid component with one or more specific reagents. Such diagnostic evaluation, primarily for different anomalies, has been the focus of increasingly refined clinical techniques and devices.

A particularly important and very frequently tested body fluid is blood plasma, most often obtained in hospital practice by venipuncture followed by withdrawal of 5 cc or more of blood, which in turn is spun in a centrifuge. The red cells settle to the tube bottom, leaving the clear plasma in the upper portion. This procedure entails the usual hazards of venipuncture, and is not generally feasible in other than hospital environments. Many test procedures require as little as 5 microliters ($\mu$L), or about 1/5th to 1/10th of the volume of a drop of blood. The subject invention is addressed to methods and devices which provide convenient and economical means for obtaining about 3 to 30 $\mu$L of plasma, and to combinations thereof with the other components of diagnostic devices.

It is important in such tests to assure an absence of substances interfering with the target analyte. It is equally important that the plasma be obtained with all of its components present, and with an undetectable level of removal during the separation. For example, none of the factors I through XII (which constitute a cascade essential to the clotting of blood) should be significantly diminished from their original concentration in the blood plasma. If the separation is accomplished by passage through fine fibrous media, a number of these and of other factors, such as hormones, proteins, nucleic acids, enzymes, growth factors, lipoproteins, and other important normal and abnormal blood components such as heparin tend to be removed by adsorption to the fiber surfaces.

Further, it is highly desirable that components of the immune system, including the numerous proteins which constitute complement, be neither removed nor activated by contact with the fiber surfaces.

Finally, hemolysis of the red cells must be avoided, as the intense red color of released hemoglobin would interfere with diagnostic tests which employ color change as a part of their procedure.

The devices and methods in accordance with this invention make it possible to obtain the quantities required for these tests from one or two drops of blood, which is readily and rapidly obtainable, for example in a doctor's office, or by an individual for himself. By using the method of this invention, the specimen so obtained is identical with or differs minimally in composition with that obtained by centrifuging.

Surface Grafted Modified Organic Fibers in Blood Product Filtration

The art of grafting organic fibrous media in the form of webs is old, and numerous variations of methods and monomers are described in the patent and technical literature; much of this art goes back 30 or more years. A substantial proportion of these references deal with methods of making the fiber surface hydrophilic, and some of these use monomers which might be expected to produce a surface graft containing hydroxyl end groups, however, none of these has been disclosed with aqueous wettability claimed to be more than merely hydrophilic; i.e. they are water wettable.

Polyester fiber mats in which the fibers have not been modified have been used for removing leucocytes from blood and blood products, particularly from packed red cells. In these, the red cells pass through the filter, while a proportion of the white cells are retained. It has been recognized that superior performance is obtained if the fiber diameter is smaller, thereby increasing the area of the fiber surfaces and enhancing white cell removal efficiency. Fibers made by the melt blowing process can be processed into webs with average fiber diameter below three micrometers ($\mu$m), while the finest conventional process (extruded and drawn) fiber currently available has a diameter of about 6 to 7 $\mu$m, hence with less than half the surface area. Melt blown fibers are accordingly preferred for these blood filters.

An improved version of melt blown polyester fiber filters for removal of white cells while passing red cells is described in U.S. Pat. No. 4,923,620 in which the fibers are surface modified by grafting to a level of aqueous wettability higher than that of unmodified polyester fiber, but in the most preferred form below the level of being hydrophilic.

In U.S. Pat. No. 4,880,548 which is directed to the filtration of platelet concentrate derived from blood, the filter passes platelets freely while removing white cells. This filter also employs surface grafted melt blown polyester fibers, in this case surface grafted to obtain a CWST preferably in excess of 90 dynes/cm, and more preferably a CWST of at least 95 dynes/cm (see below for a definition of CWST).

In order to define the filters of the above noted U.S. patents in a manner such that they could be duplicated by others, it was necessary to invent a novel means for measuring the wettability of membranes; that means is substantive to the subject invention, and is for this reason described below.

Wetting of Fibrous Media

When a liquid is brought into contact with the upstream surface of a porous medium and a small pressure differential is applied, flow into and through the porous medium may or may not occur. A condition in which no flow occurs is that in which the liquid does not wet the material of which the porous structure is made.

A series of liquids can be prepared, each with a surface tension of about 3 dynes/cm higher compared with the one preceding. A drop of each may then be placed on a porous surface and observed to determine whether it is absorbed quickly, or remains on the surface. For example, applying this technique to a 0.2 micrometer porous polytetrafluoroethylene (PTFE) filter sheet, instant wetting was observed for a liquid with a surface tension of 26 dynes/cm. However, the structure remained unwetted when a liquid with a surface tension of 29 dynes/cm was applied.

Similar behavior is observed for porous media made using other synthetic resins, with the wet-unwet values dependent principally on the surface characteristics of the material from which the porous medium is made, and secondarily, on the pore size characteristics of the porous medium. For example, fibrous polyester (specifically polybutylene terephthalate (hereinafter "PBT") sheets) which have pore diameters less than about twenty micrometers is wetted by a liquid with a surface tension of 50 dynes/cm, but is not wetted by a liquid with a surface tension of 54 dynes/cm.

In order to characterize this behavior of a porous medium, the term "critical wetting surface tension" (CWST) has been defined as described below. The CWST of a porous medium may be determined by individually applying to its surface, preferably dropwise, a series of liquids with surface tensions varying by 2 to 4 dynes/cm, and observing the absorption or non-absorption of each liquid. The CWST of a porous medium, in units of dynes/cm, is defined as the mean value of the surface tension of the liquid which is absorbed and that of a liquid of neighboring surface tension which is not absorbed. Thus, in the examples of the two preceding paragraphs, the CWST's were respectively 27.5 and 52 dynes/cm.

In measuring CWST, a series of standard liquids for testing are prepared with surface tensions varying in a sequential manner by 2 to 4 dynes/cm. Ten drops of each of at least two of the sequential surface tension standard liquids are independently placed on representative portions of the porous medium and allowed to stand for 10 minutes. Observation is made after 10 minutes. Wetting is defined as absorption into or obvious wetting of the porous medium by at least nine of the ten drops within 10 minutes. Non-wetting is defined by non-absorption or non-wetting of at least nine of the ten drops in 10 minutes. Testing is continued using liquids of successively higher or lower surface tension, until a pair has been identified, one wetting and one non-wetting, which are the most closely spaced in surface tension. The CWST is then within that range and, for convenience, the average of the two surface tensions is used as a single number to specify the CWST.

Appropriate solutions with varying surface tension can be prepared in a variety of ways, however, those used in the development of the product described herein were:

| Solution or fluid | Surface Tension, dynes/cm |
|---|---|
| Sodium hydroxide in water | 94–110 |
| Calcium chloride in water | 90–94 |

-continued

| Solution or fluid | Surface Tension, dynes/cm |
|---|---|
| Sodium nitrate in water | 75–87 |
| Pure water | 72.4 |
| Acetic acid in water | 38–69 |
| Ethanol in water | 22–35 |
| n-Hexane | 18.4 |
| FC77 (3M Corp.) | 15 |
| FC84 (3M Corp.) | 13 |

By the above described means the previously used terms to describe wettability of porous media are, for the first time, clearly defined. To describe a porous material as hydrophilic is not definitive, because its CWST could, by that definition be anything between 73 and 110 or higher, yet the behavior in many applications of a medium with a higher CWST value is very different from that of one with a CWST of 73 dynes/cm.

Wetting of Fibrous Media by Blood

In packed red cells, as well as in whole blood, the red cells are suspended in blood plasma, which has a surface tension of 73 dynes/cm. Hence, if plasma is placed in contact with a porous medium, spontaneous wetting will occur if the porous medium has a CWST of 73 dynes/cm or higher.

The surface tension of the red cell surfaces is given in the literature as 64.5 dynes/cm. ("Measurement of Surface Tensions of Blood Cells & Proteins", by A.W. Neumann et al., from Annals N.Y.A.S., 1983, pp. 276–297.) The hematocrit of blood, i.e. the percent by volume of the blood occupied by the red cells, generally ranges from 37 to 54%, and this concentration is sufficient to cause whole blood to wet porous media with CWST values above about 64 to 65 dynes/cm.

BRIEF DESCRIPTION OF THE DRAWINGS

FIG. 1 is a schematic side view of a test apparatus used in certain of the examples.

FIG. 2 is a schematic side view of a device in accordance with the invention shown in cross section.

FIG. 2A is a top view of the device shown in FIG. 2.

FIG. 3 is a perspective of another device in accordance with the invention.

FIG. 4 is a perspective view of still another device in accordance with the invention.

Figure 5:
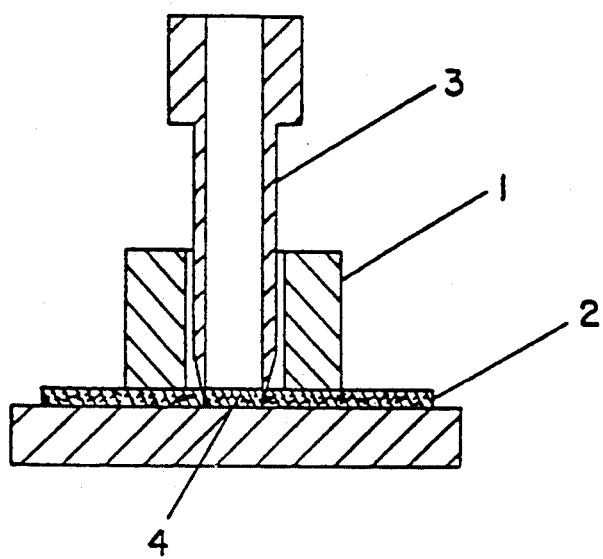
FIG. 5 is a side view in cross section of a device for cutting a disc out of a medium useful in the subject invention.

The present invention provides a device for separating plasma from blood comprising a synthetic polymeric fibrous structure having a CWST in excess of 65 dynes/cm, the structure having a first region for receiving a blood sample and a second region for accumulating plasma. The invention further provides a method for separating plasma from blood comprising contacting the blood with the fibrous structure of this device.

The present invention provides a self-contained device for the separation of plasma from blood comprising a fibrous structure having a form contained within two substantially parallel spherical surfaces intersected by a cylinder. The invention also provides a method for separating plasma from blood comprising contacting the blood with the fibrous structure of this device.

The present invention provides a device for separating plasma from blood comprising a fibrous structure in which organic fibers have been grafted to present hydroxyl groups at the filter surfaces, the device having a first region for receiving a blood sample and a second region for accumulating plasma. The invention also provides a method for separating plasma from blood comprising contacting the blood with the fibrous structure of this device.

The present invention provides a device for separating plasma from blood comprising a synthetic polymeric fibrous structure having a CWST in excess of 65 dynes/cm, and a $V_f$ of $>0.2$ cc/cc, the structure having a first region for receiving a blood sample and a second region for accumulating plasma. The invention also provides a method for separating plasma from blood comprising contacting the blood with the fibrous structure of this device.

The present invention provides a device for separating plasma from blood comprising a fibrous structure having a CWST in excess of 65 dynes/cm, the structure having a first region for receiving a blood sample, a second region for accumulating plasma, and a porous guard layer cooperatively arranged with the second region to allow passage of plasma and prevent passage of red blood cells. The invention also provides a method for separating plasma from blood comprising contacting the blood with the fibrous structure of this device.

The present invention also provides a self-contained device for separating plasma from blood and carrying out a diagnostic test comprising a fibrous structure preferably having a CWST in excess of 65 dynes/cm, the structure having a first region for receiving a blood sample, a second region for accumulating plasma, and a porous guard layer cooperatively arranged with the second region to allow passage of plasma and prevent passage of red blood cells, the porous guard layer also serving as a diagnostic medium. The present invention also provides a method for separating plasma from blood comprising contacting the blood with the fibrous structure of this device.

The present invention provides a self-contained device for separating plasma from blood and carrying out a diagnostic test comprising a fibrous structure having a CWST in excess of 65 dynes/cm, the structure having a first region for receiving a blood sample, an outwardly extending second region for accumulating plasma, a portion of the first region adjacent to the outwardly extending portion having been compressed to greater density, cooperatively arranged to allow passage of plasma and prevent passage of the red blood cells, the second region serving optionally as a diagnostic medium. The present invention also provides a method for separating plasma from blood comprising contacting the blood with the fibrous structure of this device.

The present invention provides a method for separating plasma from blood comprising contacting a first region of a synthetic polymeric fibrous structure having a CWST in excess of 65 dynes/cm with a blood sample.

DISCLOSURE OF THE INVENTION

In accordance with the subject invention, devices and methods for separating microliter quantities of plasma from whole blood are provided.

The invention provides a method for obtaining clear plasma from quantities of blood of the order of about 50 to 100 microliters, whereby the blood is applied to a designated portion of a porous fibrous mat, and a short time thereafter clear plasma appears in another portion of the fibrous mat, from which the plasma can be removed by contacting it with a porous medium of smaller pore size and hence of higher capillarity.

The synthetic, polymeric fibrous structures in accordance with the subject invention preferably comprise any of the resins which can be successfully used to form cohesive webs using the melt blowing process. These include polybutylene terephthalate, polyethylene terephthalate, polymethyl pentene, polypropylene, polyethylene, any of a number of polyamides, and polycarbonates, as well as any of a number of less commonly used resins. All fibrous mats made from these polymers have CWST below about 46 dynes/cm, and for use in this invention fibers made therefrom must be surface grafted to raise their CWST to above about 65 dynes/cm, and preferably above 95 dynes/cm, more preferably above 110 dynes per cm.

If it is desired that the composition of the segregated plasma retain all of the components present in the plasma of the blood, the graft should be such as to produce on the fiber surfaces the highest possible density of hydroxyl groups, mixture of hydroxyl and carboxyl groups, mixture of hydroxyl and methyl groups, or amine groups. In the process of this invention, this is accomplished by the use of monomers presenting hydroxyl groups, and polymerizing these in an aqueous environment. Selection of monomers and of conditions for grafting is readily possible for persons familiar with the art. A criterion for selecting webs least likely to remove plasma components is the highest possible CWST. A CWST in excess of 65 dynes/cm, and preferably in excess of 110 dynes/cm is a criterion for a preferred product of this invention.

Devices Employing the Method of this Invention

The direction of motion from the location or region at which the blood is added to the location at which the clear plasma appears is an important design factor, and is referred to hereinafter as the flow direction.

The melt blowing process for making fibrous webs employs fiberizing nozzles comprising two or more passages, of which the innermost passage delivers softened or molten resin to the tip of the nozzle, while the others deliver a gas, usually air, at high velocity, which attenuates the resin to form fibers. In a preferred form of the invention, the fibers are then collected and form a web on a moving collector surface usually located about 5 to 25 centimeters from the nozzle tip. In order to obtain a high degree of orientation, the velocity of the moving collector surface should be in excess of about 10 meters/minute. At this collector speed the weight of fiber collected per unit area tends to be small, generally between about one tenth to one hundredth of the thickness required for devices employing the method of the subject invention, thus up to about 100 layers of medium may be required.

When highly oriented mats are used, very different results are obtained depending on the orientation of the web with respect to the plasma direction.

Preforming of Media to Integral Shapes

The multiple layers produced as described above can be passed through a laminating oven, which may consist of two moving belts which convey the product through an oven, in which pressure rolls form the medium to the required density. This operation bonds the layers to form a single integral sheet, which can then be cut to the required sizes for use in a plasma separating device of the subject invention. Surface grafting to the desired condition can be done either before or after laminating. Layups can also be preformed to form laminated sheets by compressing between hot platens. Heated dies may be used to obtain special shapes, and to vary the pore size between adjacent areas.

Media previously available for plasma separation have used glass fiber mats. Glass fibers are, however, very difficult to work with. In order to obtain uniformity the fibers must be laid down from aqueous suspension, and the process is such that there is little latitude for varying the pore size. Altering the pore size of a glass fiber mat after the mat has been formed is difficult because, if compressed lightly the mat springs back to its original thickness, while heavy compression causes fiber breakage with consequent migration of debris.

The ability of the devices of this invention to be made as calendered sheet and in preformed shapes by hot forming is a feature of this invention.

Multilayer mats of fiber diameter under about 3 μm can also be cold formed, with a somewhat lesser degree of adhesive integrity, which is nevertheless sufficient for some applications.

Modes of Use of Plasma Separation Media

The basic function of the media used in the process of the subject invention is to deliver to one section of the porous medium clear plasma derived from another section which has been contacted by blood.

That is, media in accordance with this invention comprise first and second regions, a first region where blood is applied and a second region where plasma is concentrated during the separation process via a plasma front advancing ahead of the red cell boundary. In preferred embodiments of the invention, the media is secured to a holder for facile manipulation of the media, e.g., during contacting of the second region where the plasma is concentrated with another medium such as a membrane for carrying out a diagnostic test. The subject invention is also directed to such combinations.

Figure 7:
FIG. 7 is a side view in cross section of the disc after formation into the desired shape of a cupped disc.
Figure 9:
FIG. 9 is a side view in cross section showing a variant of the cupped disc of FIG. 7, a cupped disc with a flat lower surface.

To aid in handling the devices according to the invention, particularly the cupped discs shown in FIGS. 7 and 9, the device may optionally include an extension portion attached to the edge of the device, thus providing a handle for manipulating the device after it has been wetted by blood. For example, the end of a polyethylene strip may be melted, and the molten end contacted to the edge of the cup or device, providing after the molten resin has cooled and become solid, a convenient handle whereby the cupped disc can be manipulated into place prior to use, and removed after use while avoiding contact of the user's fingers with the red cells and plasma.

The plasma so concentrated can be used in a number of ways. It can be subjected to a diagnostic test as it is collected, for example by preplacing a reagent in the plasma separating medium, and observing for example a change in color of the collected plasma. Alternately, the plasma collecting area can be placed in contact with one or more hydrophilic filters or membranes of pore size smaller than that of the plasma separation device, whereby the plasma wicks onto the membrane(s), generating a color or other signal on the membrane. The membrane(s) may have been pretreated, for example, with antibodies. The membrane(s) may be placed in contact with an absorbent pad, or placed over an evacuable chamber, allowing water or an aqueous reagent solution to wash, or to react with the contents of the membrane. These types of applications can take numerous forms, some of which are described in the examples.

Because of its simplicity and universality of application, one mode of particular interest is the plasma separation device used independently of the membrane. Such devices are illustrated in FIGS. 2, 3, 7, 8 and 9. Blood is placed at one end of the device, and the red cells and plasma migrate to the opposite end, which may project slightly. A portion of the plasma advances ahead of the red cell boundary as the fluids advance toward the opposite end until the red cell boundary is observed to stop, signalling that the section of the filter beyond the red cell boundary has been filled with plasma. The plasma end may then be placed in contact with a membrane, whereby the plasma is rapidly absorbed by the membrane. Properly designed, the time span between application of blood and the completion of saturation of the membrane is less than about one minute.

This mode is particularly advantageous because of its convenience; the same separator-applicator device can be used with membranes of a range of sizes and with varied pretreatment. A second advantage is that the progress of the red cell boundary can be observed visually, and the device removed to prevent red cells from reaching the membrane. A third advantage is that the blood containing applicator can be discarded while tests continue on the membrane—a not negligible advantage in view of the current prevalence of blood transmitted diseases.

EXAMPLES

Fiber diameters presented were derived from BET fiber surface area measurements, using the equation $$d = \frac{4}{DA}$$

where
d = average fiber diameter
D = density of the fibers
A = BET surface area expressed as square meters per gram In presenting the data of the examples of this invention, the term $V_f$ has been used to represent the ratio of the volume of the fibers to the volume of the filter mat.

The use of this term to characterize the mat is more meaningful than the use of density, especially when comparing media made using fibers of differing densities. For example, the products of this invention can be made using similarly grafted PBT and polypropylene fibers, each made with $V_f=0.2$. These would have equal average pore size, and would behave similarly for plasma separation, but the mat densities would be very different.

The following table illustrates further the distortion introduced by defining media characteristics by density:

| Material | Fiber Density, g/cc | Mat Density, g/cc | $V_f$ cc/cc |
|---|---|---|---|
| Polypropylene | 0.90 | 0.180 | 0.2 |
| PBT | 1.38 | 0.276 | 0.2 |
| Glass | 2.50 | 0.500 | 0.2 |

PBT web used in the examples was made by melt blowing and collecting the fibers as a web. For use in examples 1, 2, 4, 7 and 10, the web was grafted using Cobalt 80 radiation with, unless otherwise noted hydroxyethyl methacrylate (HEMA) as the monomer, in an aqueous milieu, the product after washing and drying having a fiber diameter of 2.6 μm, an estimated density of 1.36 g/cc, and a weight of 0.00138 grams/square centimeter (g/cm$^2$).

For examples 1 and 2, a test apparatus was constructed of transparent plastic as shown in FIG. 1, in which the top plate 1 was 2.5 cm wide, 8 cm long and about 1.5 cm thick, and provided a flat surface 2. The mating member 3 provided an opposed flat surface 4 which is 3 cm wide.

In order to prepare example 1a, seven layers of the 0.00138 g/cm$^2$ web were laid one on the other, and strips were cut parallel to the fiber orientation to 0.44 cm wide×2.58 cm long. In order to run a test, the strip 6 was placed on surface 4 perpendicular to the length of the apparatus of FIG. 1, and the spacing of the two plates adjusted by means of the two screws 7 (the second not shown) to compress the strip 6 to 0.054 cm. Blood was then added from a pipet at 5, while observing the motion of the red cell and plasma boundaries through a reticle equipped microscope. When the red cell boundary became stationary, indicating that all of the pores of the test strip 6 had been filled, the position of the red cell boundary was recorded.

Referring now to Table 1, in order to perform example 1a, the specimen thickness was adjusted to 0.054 cm. Based on the known fiber weight, the fiber density, and the specimen volume, the ratio of fiber volume to total volume, $V_f$, is 0.13 cc/cc. Multiplying the specimen length by its width and thickness yields the total specimen volume, and multiplying that figure in turn by $(1-V_f)$ yields the volume of voids in the specimen, which is 0.0205 cc, or 20.5 μL. This volume can be assumed to be equal to the volume of blood supplied to the specimen. The volume of plasma collected (2.2 μL for example 1a) divided by the volume of blood supplied and multiplied by 100 yields the plasma recovery efficiency of 10.8%. Examples 1b to 1g were run in similar fashion, with the appropriate number of layers of the web used for each.

TABLE 1

Plasma Separation Efficiency as a Function of Fiber Fractional Volume $V_f$. Oriented fibers with flow parallel to fiber direction. Specimen length = 2.58 cm, width = 0.44 cm. Apparatus of FIG. 1. Blood drawn into EDTA anticoagulant. Hematocrit = 39 ± 1%.

| Example No. | Specimen thickness, cm | $V_f$ cc/cc | Time sec. | Voids Volume μL | Volume of plasma collected, μL | Plasma recovery efficiency, % |
|---|---|---|---|---|---|---|
| 1a | .054 | 0.13 | 81 | 20.5 | 2.2 | 10.8 |
| 1b | .056 | 0.16 | 90 | 20.5 | 2.9 | 14.3 |
| 1c | .056 | 0.20 | 105 | 19.6 | 4.3 | 22.0 |
| 1d | .058 | 0.24 | 120 | 19.3 | 5.0 | 25.9 |
| 1e | .064 | 0.27 | 116 | 20.4 | 6.3 | 30.9 |
| 1f | .066 | 0.30 | 352 | 20.0 | 8.4 | 41.8 |
| 1g | .073 | 0.38 | 580 | 20.0 | 10.7 | 53.2 |

Webs with lower $V_f$ values have lower efficiency, and for this reason are less preferred. Webs with $V_f$ values in excess of 0.20 are preferred, while webs with $V_f$ greater than 0.24 are more preferred.

Example 2 was performed in the manner of and using the materials and the apparatus of Example 1, and serves to compare the serum separation behavior of otherwise equal strips when cut such that the flow direction is parallel with or perpendicular to the direction of fiber orientation. The results are shown in Table 2.

TABLE 2

Plasma separation with flow parallel and perpendicular to fiber orientation. Conditions otherwise as noted for Table 1.

| Orientation | Specmen thickness, cm | $V_f$ cc/cc | Time sec. | Voids Volume μL | Volume of plasma collected, μL | Plasma recovery efficiency, % |
|---|---|---|---|---|---|---|
| Parallel | .054 | 0.16 | 109 | 20.4 | 3.4 | 16.6* |
| Parallel | .056 | 0.20 | 104 | 20.5 | 3.8 | 19.3 |
| Parallel | .056 | 0.24 | 165 | 19.0 | 4.6 | 23.6 |
| Perpendicular | .054 | 0.16 | 154 | 20.5 | 3.9 | 19.7 |
| Perpendicular | .056 | 0.20 | 233 | 20.5 | 4.5 | 22.4 |
| Perpendicular | .056 | 0.24 | 221 | 19.0 | 5.3 | 27.1 |

*The lower values compared with those of Table 1 are due to use of a different lot of blood.

The condition in which flow is directed perpendicular to the fiber orientation provides somewhat better efficiency, however, time to complete fill of the specimen is much longer. Practical consideration lead to the conclusion that both are useful; perpendicular flow is preferred for devices having a short flow path, while parallel flow is preferred for devices having a relatively longer flow path. If the target time is, for example, about one minute, devices exceeding about 0.5 to about 1 cm in length of flow path are usually best made using parallel fibers, while devices less than about 0.2 to about 0.5 cm in flow path length can best use the perpendicular flow direction.

Example 3 describes the production of a plasma separator oriented to obtain parallel flow. The working element 1 at the center of the device shown in schematic elevation in FIG. 2 is, like the filter medium of example 1, a multi-layer of fibrous web. CWST is selected to be in a preferred range. The preferred CWST range is >110 dynes/cm, which can be achieved by grafting using monomers such as HEMA, hydroxyethyl acrylate, hydroxylpropyl acrylate, or other hydroxyl presenting monomer(s). Preferred length is about 0.5 to 1.0 cm, and fiber volume, thickness and width are such as to obtain $V_f=0.24$. As in FIG. 1, the working element 1 is enclosed in a preferably clear plastic sheath 2 of oval cross section in the view perpendicular to the plane of the paper, i.e. see FIG. 2A, and is shaped such as to provide a recess 3 into which up to about 150 μL of blood can be placed. (Alternatively, the plastic sheath may have a rectangular or other cross section configuration.) After blood has been placed, flow continues for about 30 to 90 seconds until all of the voids in the mat are full, and flow then stops. The device may then be manually contacted at its projecting lower end 4 to a hydrophilic finely porous member, for example nylon 66 membrane, causing the plasma collected at the lower end of the device to be drawn into the membrane. The membrane may or may not have been pretreated with a reagent which interacts with a component of the plasma, and is generally useful for diagnostic purposes.

Example 4 describes a hot formed integral porous element. Seventeen layers of the HEMA grafted PBT web described above were hot compressed at 120° C. to a thickness of 0.064 cm and a $V_f$ value of 0.27. A test specimen was then cut from the laminate with its length parallel to the fiber orientation to obtain an integral self bonded strip 0.437 cm wide by 2.6 cm long shown in perspective as item 1 in FIG. 3. The strip was then bonded by double sided pressure sensitive tape to a polyester film backing 2. Blood was placed at 3 in contact with the end of the strip, and plasma separation observed in the manner described in example 1. Average volume of plasma collected was 5.7 μL, average efficiency was 27.7%, and average time to cessation of flow was 163 seconds.

Example 5 describes the production of a parallel flow plasma separation device with integral diagnostic capability. Melt blown web made with fiber diameter in the preferred range under 3 μm is grafted to obtain one of the preferred ranges of CWST, and then may be used as one or more layers with a total weight of 0.02 grams/cm² by hot compressing between formed platens to obtain the contour for the test strip 1 shown in FIG. 4, the thicker section being about 0.064 cm thick and about 0.5 to 1 cm long, and the thinner section about 0.042 cm thick×0.5 cm long. The two sections thus have $V_f$ respectively about 0.27 and 0.41 cc/cc. The test strip 1 is bonded to a plastic backing 2 in the manner of example 4. Blood is applied to the end of the strip at 3 and after about one minute plasma reaches the higher $V_f$ section 4, where it is absorbed due to its higher capillarity. Section 4, which may or may not have been preimpregnated with a diagnostic reagent, is used for diagnostic purposes.

In example 6, the thinner, more dense section of the hot compressed preform (test strip) of example 5 is preimpregnated with a reagent, whose purpose is to interact with blood plasma to provide diagnostic information.

Example 7 describes an economical and easy to use plasma separating device. Melt blown fibrous web was prepared with a fiber diameter of 2.4 μm at a weight of 0.0013 grams per cm². After γ-grafting with HEMA monomer, washing and drying, CWST was greater than 110 dynes/cm, fiber diameter was 2.6 μm, and weight was 0.00138 g/cm . Sixty-four layers of this medium were laid one on the other and hot compressed between steel platens heated to 120° C. to a thickness of 0.27 cm.

Figure 6:
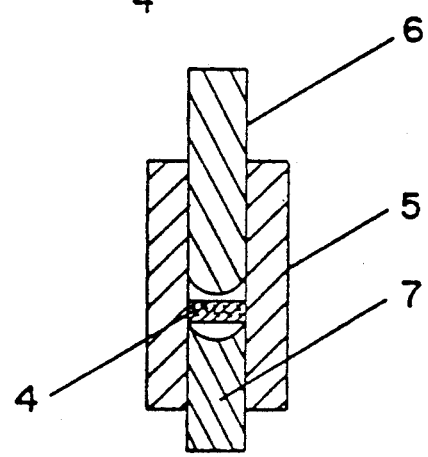
FIG. 6 is a side view in cross section of a device for forming the disc into the desired shape.

As shown in FIG. 5, a steel hollow cylinder "hold down" 1 about 3 cm outside diameter, 1 cm inside diameter and 3 cm long was used to lightly compress the porous medium 2 while the sharpened end of a cylindrical cutting tool 3 of inside diameter 0.794 cm and outside diameter 965 cm was inserted into the 1 cm inside diameter of hold down 1 and rotated to cut a disc 0.794 cm diameter. The disc 4 was then transferred as shown in FIG. 6 to a second steel hollow cylinder 5 of id 0.797 cm and length about 3 cm. A steel rod 6 of outside diameter 0.795 cm was formed at one end to a convex 0.476 cm spherical radius, and a second such rod 7 was formed at one end to a concave 0.476 spherical radius. The two rods were inserted into the 0.797 cm diameter cylinder 5, and a force of 11 Kg was applied to the rod ends to form the disc 4 into a cup shaped member. The product is shown in vertical cross section as item 8 in FIG. 7, in which the cross sectioned (hatched) portion represents fiber, while the unshaded upper portion represents a near to hemispherical receptacle into which 2 or 3 drops of blood can be placed. The cupped disc 8 had an outer diameter about 0.01 cm larger than the 0.797 diameter cylinder within which it was formed, and the fibrous (shaded) portion was about 0.25 cm thick. Cohesive strength was more than adequate to withstand the manipulation incident to the procedures described below.

Using tweezers, the cupped disc was placed with its convex lower surface down on a 1.5 cm square of porous nylon 66 membrane which had been pretreated to bind organic molecules such as antibodies, enzymes, peptides, nucleic acids, and carbohydrates. 120 μL of blood was placed on the concave upper surface of the cupped disc; within about one minute, the treated nylon disc was saturated with clear plasma to a diameter of 1.3 cm. Upon removal from the nylon surface, the upper 90% of the cupped disc was seen to be saturated with red cells, while the bottom 10% remained white, being saturated with clear plasma.

An understanding of the advantages of the cupped disc 8 may be obtained by comparing it with a simple right circular disc used for the same purpose:

(a) The full volume of even one drop of blood is likely to overflow the edges of a simple disc, aborting the procedure. The cupped disc accepts 2 or more drops comfortably.

(b) By filling the cup, its whole upper surface is uniformly exposed to the blood, resulting in more efficient separation, a larger volume of plasma, and faster completion of the operation.

Other advantages of the cupped disc are described in example 10.

The three step process described above in which a laminate is hot formed, then cut to disc form, then shaped to form a cup, may be combined into one by first preheating the layup, for example by passing hot air through it, and while still hot, cutting a disc and sequentially in the same operation compressing and forming the finished cupped disc.

A stronger, more coherent cupped disc, more resistant to mechanical damage during storage, shipping and use, can be obtained by modifying the procedure of example 7 as follows: (a) The fibers of the melt blown web are surface grafted, and the web is then water washed, (b) the wet web is laid up and processed to form a cupped disc as described in example 7, (c) the formed cup is then dried by application of heat thereto.

It should be noted that in example 7 flow is perpendicular to the fiber orientation. Further, the shape of the device of this embodiment may be described as "contained within two parallel (not concentric) spherical surfaces intersected by a cylinder", however, it should be understood that minor deviations from parallelism fall within the purview of this embodiment of the invention.

Example 8 describes a variant of Example 7. As shown in FIG. 9, this variant is distinguished by presenting a flat lower surface. This is advantageous when the device is used for its intended function, as it will deliver plasma faster, and provide a better yield of plasma, while at the same time providing a receptacle for the applied blood as does example 7.

EXAMPLE 9

The Devices of Example 7 Incorporating Two Reagents

Diagnostic procedures often require that a first reagent be added to the plasma before it contacts a second reagent, the second reagent having been covalently or ionically bonded for example, to a finely porous polyamide membrane in a pretreatment step. In order to provide the first reagent, eight layers of the 1.2 mg/cm$^2$ HEMA grafted melt blown web are pretreated by saturation with a solution of the first reagent, and then allowed to dry. Separately, 56 layers of HEMA grafted melt blown web are hot compressed at 120° C. to a thickness of about 0.28 cm, and the two layers are then combined and formed to a cup shape as described in example 7 (FIG. 7), or to the flatter configuration of example 8 (FIG. 9), with the impregnated portion on the lower face. The proportion of pretreated layers may vary from zero to 100%, and about 10 to about 100 total layers may be used. Hot compression can be performed in the range of about 120° to 170° C., thickness of the device may vary from about 0.15 to about 0.35 cm, and the pretreated layers may vary from about 5 to 50% of the total thickness.

When the resulting composite device is used in the manner of examples 7 or 8, the first reagent dissolves in the plasma as it diffuses through the lower portion of the device, and then contacts the second reagent in the membrane, providing a diagnostic signal, such as a color change, of the membrane.

In an alternate arrangement, both the first and second reagents may be contained in the device in successive layers, and the product of the resulting reaction is adsorbed by a membrane, providing a diagnostic signal.

EXAMPLE 10

Making an Enclosed Cupped Plasma Separating Device

Figure 8:
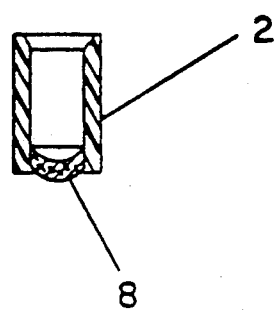
FIG. 8 is a side view in cross section of a cupped disc as shown in FIG. 7 positioned in a plastic tube, the combination being a device in accordance with the subject invention.

As shown in FIG. 8, a cupped disc 8 made as described in example 7 was ejected from the second steel cylinder 5 of FIG. 6 directly into a plastic tube 2 of inside diameter 0.79 cm and outside diameter 0.95 cm. The tube comprised an internal flange at its lower end, which served to locate the disc such that its convex lower surface projected from the bottom of the tube, as shown in FIG. 8. The 2 cm length of the tube 2 permitted it to be easily grasped by the thumb and forefinger.

Blood was placed onto the upper concave portion of the disc 8, and the tubular assembly was then firmly placed on a finely porous hydrophilic pretreated membrane disc. In the placement step, the cupped disc was forced upward, such that the bottom of the tube 2 rested squarely on the surface of the membrane, and caused a relatively larger area of the bottom of the disc to be in intimate contact with the membrane, thereby accelerating absorption of the plasma.

Compared with the device of FIG. 7, the device of FIG. 8 provides a more rugged test assembly, requires less care in packaging and during storage and use, speeds up the test process, and obviates the need for tweezers to manipulate the separation device of example 7. Still another advantage of this device is that the blood may be conveniently delivered to the disc by using standard microhematocrit (MH) tubes. The MH tube is filled by contacting it to blood oozing from a finger prick, and placed in the plastic tube with its end in contact with the cupped disc, where it then rests freely at a small angle from vertical until emptied by the capillarity of the disc. The same MH tube, or another, may if necessary then be refilled to obtain the required quantity of plasma in the membrane.

All of the above advantages, together with the added advantages described under Example 8, are obtained by inserting the device of example 8 (FIG. 9) into a tube in the manner described above.

In addition to the above noted advantages, use of a cupped disc obviates the need for a leak tight seal to the tube wall, as would be needed with a simple right circular disc. A further advantage is that the cup shape provides secure retention in an internally flanged cylinder; a simple disc used with a flange would not contact an underlying membrane. If the cup is such that its outer diameter is near to vertical at the rim, it may be provided with an outwardly extending flange, which in assembly serves to retain the cup in the plastic tube.

Example 11 is a cupped plasma separating device with an abrasion resistant lower surface. The device of example 8 (FIG. 9) is made with the application to the lower face of a thin flexible relatively more abrasion resistant porous layer of higher density, which may for example be made by hot calendering melt blown web, or by using a woven or non-woven fabric. The applied layer is preferably hydrophilic and more preferably has a CWST in excess of 110 dynes per cm.

Example 12 describes the characteristics of 2.4 $\mu$m fiber diameter PBT melt blown web grafted with monomers which present surface groups other than hydroxyl. Test strips of these media were prepared at the same weight and V$_f$ as example 1d, and were tested in the manner of example 1d.

Example 12a was grafted to present a mixture of carboxyl and hydroxyl groups, and tested in the sodium salt form. It had a CWST of 96 dynes/cm; the best of several results obtained had an average separation efficiency of 14.3%.

Example 12b, grafted to obtain fibers presenting an amine group had a CWST of 75 dynes/cm, and an average efficiency of 15.7%.

Example 12c, grafted to obtain fibers presenting hydroxyl groups together with a predominant number of methyl groups, had a CWST of 66 dynes/cm, and an average efficiency of 15.6%.

The above efficiencies may be compared in column 5 of Table 3 below with example 1d, which at 25.9% is substantially better.

EXAMPLE 13

Negligibly Low Removal of Blood Components from Plasma

In many or most of the diagnostic procedures performed on blood plasma, it is preferred by the user that the separation device remove negligibly small quantities of normal or abnormal components from blood. This is preferably accomplished by the devices in accordance with the subject invention which have been grafted to present densely packed hydroxyl groups at the fiber surfaces, and which have CWST greater than 110 dynes/cm.

A widely accepted test procedure used to determine the quantity of physiological protein removed by passage through a filter uses a radioactively labelled solution of bovine serum albumin (BSA). A low score on this test, e.g. adsorption by the filter of less than about 10 micrograms ($\mu$g) of protein from 250 $\mu$g of incident protein, indicates that for most purposes the level of protein adsorption is negligibly low.

The test is run using radioactively labelled BSA as follows:

A solution containing 0.1 mg/ml of unlabelled BSA and about $10^5$ cpm/ml $^{125}$I-labelled BSA is prepared in a phosphate buffered saline (PBS) solution contained 0.2 grams per liter of monobasic sodium phosphate and 8.77 grams per liter sodium chloride in deionized water.

A sample of a porous test medium is placed in a syringe-type filter holder. Fluid communication between a reservoir holding the BSA test solution and the syringe-type filter is provided by a length of Tygon (a trademark of Norton Company) tubing and a peristaltic pump arranged in series. Prior to insertion of a porous test medium sample into the filter holder, any non-specific protein binding sites present on both the tubing and the filter holder are equilibrated by recirculating 1.0 ml of the BSA solution through the tubing and filter holder at a flow rate of 0.3 ml/min for a period of 15 minutes. Following recirculation, the BSA solution is drained from the tubing and filter holder. Residual BSA solution is removed from the tubing and filter holder by circulating about 2.0 ml of PBS through the tubing and filter holder at a flow rate of about 0.3 ml/min for several minutes at ambient temperature.

A 13 mm diameter disc of the test medium is assembled into the filter holder whose gasket inner dimension defines a filter area of 0.64 square cm. The $^{125}$I-BSA solution is then transferred from the reservoir to the filter holder at a flow rate of 0.8 ml/min/cm². The test is continued for a period of 5 minutes, during which time 250 micrograms of BSA is passed through the filter holder. A volume of 2.5 cc of PBS is then passed to clear radioactive fluid retained in the disc. The test medium is then removed from the filter holder and blotted dry on filter paper. The amount of protein (BSA) adsorbed by the test disc is determined by radioactive counting in a gamma counter.

The above described test was run twice on each of the media listed in Table 3 with the average results shown in column 4:

TABLE 3

| 1<br>Example No. | 2<br>Medium | 3<br>CWST | 4<br>Average adsorption of albumin $\mu$g | 5<br>Plasma Recovery efficiency, % |
|---|---|---|---|---|
| 1d | OH grafted | >110 | 7.9 | 25.9 |
| 12a | OH + COOH* grafted | 95 | 13.6 | 14.3 |
| 12b | amine grafted | 75 | 13.0 | 15.7 |
| 12c | OH + CH$_3$ grafted | 66 | 37.0 | 15.6 |

*In the form of the sodium salt

Taking into account both plasma recovery efficiency and protein absorption, the product corresponding to example 1d is most preferred, those 12a and 12b are less preferred, and that of 12c still less preferred.

EXAMPLE 14

In like manner to Examples 7 and 9, a plasma separating device having the configuration shown in FIGS. 10 and 11 was prepared as follows:

Sixty-four layers of the medium described in Example 7 were in like manner laid one on the other. A prewet, hydrophilic nylon 66 microporous membrane having a pore size of 0.45 $\mu$m and a thickness of 0.0076 cm was then placed under the layered stack and, using the cutting device shown in FIG. 5, a disc 0.794 cm in diameter was cut from the 65 layer stack. The cut disc was then transferred to a forming device similar to that shown in FIG. 6 except that the lower steel rod (corresponding to 7 in FIG. 6) had an upper surface such as to form the lower surface 4 of the device 1 with a substantially flat form as shown in FIGS. 10 and 11. Prior to compression under a force of 22.7 Kg, the disc structure was saturated with water by placing about 0.2 cm³ of water in the device.

Figure 11:
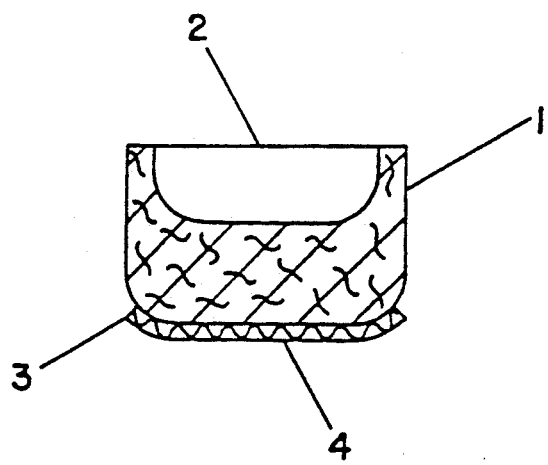
FIG. 11 is an enlarged view of the cupped disc of FIG. 10 permitting the membrane layer to be more readily seen.
Figure 12:
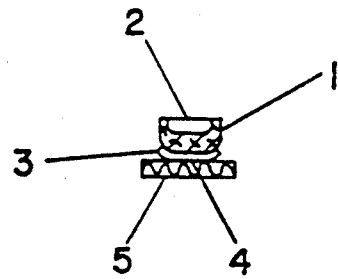
FIG. 12 is a side view in cross section showing the cupped disc of FIGS. 10 and 11 assembled to a second membrane disc.

After compression the device 1 was removed from the forming device and dried. The nylon disc conformed to the lower surface of the cupped disc and was firmly bonded thereto. The resulting plasma separation device 1 had the configuration shown in FIG. 11 with an upper recess 2, a bottom membrane layer 3 with a lower or bottom surface 4. After drying the cupped disc was placed as shown in FIG. 12 on a 1.12 cm diameter tared disc of 0.016 cm thick 0.2 $\mu$m nylon 66 membrane 5, and 130 microliters of blood was placed in the recess 2. Within 60 seconds the flow of blood had appeared to cease, with only a small quantity of blood remaining in the recess 2. After two additional minutes plasma had wicked into disc 5, and it was removed, reweighed and found to have absorbed 14.3 milligrams (mg) of plasma. The volume of plasma in disc 5 was calculated using the specific gravity of plasma (1.024) and found to be 14 $\mu$L. The pore volume of disc 5 was calculated to be 14 $\mu$L, indicating complete filling of the pores of disc 5.

When put in place prior to the addition of blood, membrane layer 3 and disc 5 were pure white in color; after completion of the test they were still pure white, i.e., no change in color could be observed. This indicates a zero or very low level of hemolysis, and zero passage of red cells through membrane layer 3.

In embodiments of the subject invention such as that described in Example 14, membrane layer 3 serves several purposes. First, this layer acts as a barrier or guard layer, guarding against the passage of red cells into the region where a diagnostic test may be performed, i.e., either on surface 4 of membrane layer 3, or on the finer pored nylon disc 5. Providing a barrier to red cell passage, with no hemolysis, is an important function of the final layer. In the absence of the layer, if an excess of blood were applied to the separation device of FIG. 12, the red cell front would continue to advance into the region defined by disc 5, where it would interfere with a diagnostic procedure. The guard layer makes the device tolerant of the addition of excess blood, and obviates the need for carefully matching the volume of added blood to the pore volume of the device, thereby making the use of the device easier and faster.

Secondly, by acting as a barrier to the passage of red cells the lower surface of the guard layer can itself be used as a diagnostic medium.

As a third benefit, the membrane guard layer, which is non-fibrous, provides abrasion resistance and additional strength in a manner similar to the device described in Example 11.

It should be noted that, while reference is made in Example 14 to the membrane layer 3 as a lower or bottom layer, the use of a layer to provide the benefits described above is not limited to cupped discs and other devices similar in configuration to examples 7, 8, 9, 10, 11, and 14. For example, in the configuration of Example 3, as shown in FIG. 2, the tip 4 can be enclosed with a membrane guard layer.

The characteristics described above for the membrane layer are best provided by hydrophilic, microporous membranes with pore sizes of from about 0.1 to about 1.0 micrometer(s). Preferably, the guard layer is no thicker than about 0.015 cm, and more preferably is less than 0.010 cm thick. Nylon 66 membranes are particularly preferred. Other microporous membranes may also be used as well as other porous structures having the requisite characteristics, and are, or have been modified to be wettable by plasma.

Preferably, the guard layer has a larger pore size than a diagnostic medium to which it delivers plasma, as the transfer of plasma is facilitated by the higher capillary attraction of a finer pored diagnostic medium. In this way, the plasma contained in the guard layer is "sucked out" into the finer pored layer, to which the plasma is delivered. For example, as may be seen in Example 14, plasma wicks from the 0.45 $\mu$m guard membrane 3 into the 0.2 $\mu$m diagnostic membrane 5.

EXAMPLE 15

Figure 10:
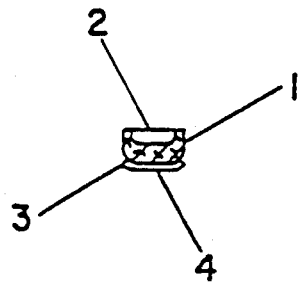
FIG. 10 is a side view in cross-section showing a variant of the cupped disc of FIG. 9 with a membrane guard layer positioned across the lower side.

A flat bottom cupped disc is made in the manner of example 14, except that the membrane disc 3 of FIG. 10 has been grafted in the manner described in U.S. patent application Ser. No. 945,569, filed Dec. 23, 1986, which is incorporated herein by reference. A test for removal of blood components is run in the manner of Example 13. The calculated BSA adsorption is increased by less than 2%, an increase within the experimental error of the BSA adsorption test.

EXAMPLE 16

A disc of microporous, hydrophilic nylon 66 membrane, made in accordance with U.S. Pat. No. 4,340,479 is processed in accordance with the procedure of U.S. Pat. No. 4,693,985 whereby it becomes capable of readily binding to a variety of proteins, antibodies, and other organic molecules useful in diagnostic procedures. The disc so obtained may then be exposed to a solution of a wide variety of diagnostic reagents, whereby it binds the reagent. When dried, such a disc may be saturated with plasma by substituting it in example 14 for disc 3 and/or disc 5 in FIG. 12. The patents cited in this example are incorporated herein by reference.

Example 17 describes a self contained analytical system for assaying the glucose content of blood. The device of example 14 is modified by (a) pretreating the nylon disc 3 of FIG. 10 with tetramethyl benzidine and the enzymes glucose oxidase and horseradish peroxidase, and (b) reducing the quantity of the grafted melt blown web in the device by a factor of 3 to 4 compared with example 14, whereby a single drop of 30 to 60 microliters of blood is sufficient for the test. In order to perform the test, the blood is placed into the upper recess of the cupped disc, and after about 30 seconds the cupped disc is inverted and exhibits on its nylon face 4 a blue-green color, the intensity of which is proportional to the quantity of glucose present. Similar tests using nylon pretreated with other enzymes and enzyme substrates can be used for quantifying other components of whole blood, for example cholesterol and other lipids, and serum enzymes.

Figure 13:
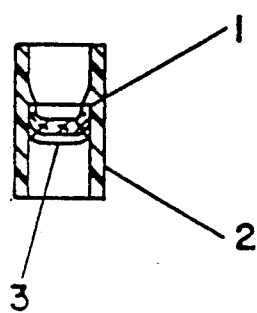
FIG. 13 is a side view in cross section showing the cupped disc of FIGS. 10 and 11 assembled into a plastic tube.

Example 18 describes a multi-stage immunological test. Nylon membrane disc 3 of FIG. 10 is pretreated with one or more specific antibodies. The cupped disc is then prepared in the manner of example 14, and is shown as item 1 of FIG. 13, centrally located within and affixed to a plastic tube (holder) 2 with membrane disc 3 facing downward. In use, (a) blood is placed into the recess of the cupped disc 1, and in less than about 30 seconds the membrane disc 3 becomes saturated with clear plasma; then (b) the tube is inverted, its lower end is connected to a controlled degree of vacuum, and a reagent is added which reacts with one or more components of the plasma bound to the antibody on membrane disc 3. This may then be followed by water or saline washing, and the application of other reagents, in accordance with the requirements of a particular diagnostic procedure. The procedure is completed by an assay step, which may visually or photometrically evaluate color change, or measure the level of radioactivity, or otherwise evaluate qualitatively or quantitatively the content of the nylon disc.

As an alternative to the use of vacuum, an absorbent pad wettable by water may be placed in the tube in contact with the recess of the cupped disc, such that reagents or washing solutions are absorbed into the pad.

EXAMPLE 19

A standard 96 well microtiter plate containing 96 open bottom holes (known as "wells") is constructed such that each well in the 8×12 array terminates in a small inwardly facing flange at its lower end. A 65 layer cupped disc such as that of Example 14 is placed at the bottom of each well, where it is retained by the flange. Using standard equipment designed for use with microtiter plates, blood samples can be delivered simultaneously to each of the wells. After about 30 to 60 seconds, special equipment available for the purpose can dispense reagents and wash, as well as evaluate and record the results for the 96 specimens of blood. Quite generally, diagnostic tests such as those described in examples 17 and 18 can be performed in multiple using a microtiter plate fitted as noted in this example.

In a variation of the above described procedure, plasma separation is accomplished using as a first layer an 11×7.5 cm multilayer melt blown web of total weight in the range of about 0.026 to about 0.1 g/cm$^2$ and with V$_f$ in the range of about 0.1 to about 0.5 and preferably with a range of 0.2 to 0.38. A second layer, consisting of a hydrophilic membrane preferably of pore size about 0.1 to 1 μm and of thickness preferably less than 0.008 cm, is bonded to the first layer, and the melt blown side of the composite is bonded to the lower end of an injection molded thermoplastic microtiter plate, forming an assembly functionally interchangeable with example 19.

A guard layer such as that described in examples 14, 15, 16, 18 and 19 can be applied with advantage to devices in which plasma separation is accomplished by glass fiber.

Such a device may incorporate, in addition to the glass fiber mat and a guard layer, a diagnostic membrane which may have been pretreated, and may also be post-treated after exposure to plasma.

The guard layer is interposed between the glass fiber mat and the diagnostic membrane, and prevents fouling of the diagnostic membrane by red cells. Alternatively, the guard layer itself may be used as the diagnostic membrane.

While a preferred form of the guard layer is polyhexamethylene adipamide (nylon 66) membrane, which when made by the process of U.S. Pat. No. 4,340,479 is hydrophilic as produced, other membranes which are not hydrophilic as produced may be used, in some cases to advantage. For example, polytetrafluoroethylene and polyvinylidene fluoride may be used if they are pretreated by grafting or by other means in order to be rendered hydrophilic, and the products so obtained provide the advantage that they are more flexible and more capable of being dimensionally extended than is nylon 66 membrane, hence can be coformed with melt blown webs to a wider range of configurations.

Other membranes which may be used as made, or if necessary to achieve hydrophilicity, after fiber surface modification, include other fluorocarbon resins, those made of nylon resins other than polyhexamethylene adipamide, such as nylon 6, nylon 610, nylon 7, nylon 11 and nylon 12, acrylics, acrylonitriles, polysulfones, polycarbonates, polyphenylene oxide and polyphenylene ether, cellulose, cellulose ester and other cellulose based plastics, acetals, various polyurethanes, various polyesters, silicones, and vinyl chloride.

EXAMPLE 20

A device modified from that described in Example 4 (and illustrated in FIG. 3) may be formed from multiple layers of HEMA-grafted PBT web and hot compressed to a desired thickness and $V_f$ value. The so formed plasma separation medium, which, for example, may be fibrous is changed in length from that shown in FIG. 3 such that its length is about one to two times its width and is then bonded, preferably by hot compression, to a porous membrane of length about twice that of the plasma separation medium or about two to four times its width, thus forming a cantilevered portion as a region for accumulating plasma. According to this example, after a sample of blood has been placed on the plasma separation medium, the plasma flow direction is first downward and generally perpendicular and then generally horizontal through the cantilevered member when blood is placed on top of the plasma separation medium, plasma appears on the cantilevered or stepped portion of the membrane. In a preferred configuration, a narrow portion of the plasma separation medium adjacent to the cantilevered portion is further compressed to reduce its thickness and increase its density, thereby providing additional assurance that red cells will be prevented from migrating out along the cantilevered membrane.

We claim:

1. A device for separating plasma from blood comprising a synthetic polymeric fibrous structure having a CWST in excess of 65 dynes/cm, the structure having a first region for receiving a blood sample and a second region for accumulating plasma, wherein the fibers in the fibrous structure have been formed to a functional shape which takes the form of two parallel or substantially parallel spherical surfaces intersected by a cylinder, thus generally resembling a cup shape having a convex end.

2. The device of claim 1 in which the rim of the functional shape includes an outwardly extending flange.

3. The device of claim 1 further comprising a cylindrical holder.

4. The device of claim 3 in which the convex end of the cup shape of the device projects beyond one end of the cylindrical holder.

5. The device of claim 3 in which at lest a portion of the bottom of the cup shape of the device projects beyond one end of the cylindrical holder.

6. A device for separating plasma from blood comprising a synthetic polymeric fibrous structure having a CWST in excess of 65 dynes/cm, the structure having a first region for receiving a blood sample and a second region for accumulating plasma, wherein the fibers in the fibrous structure have been formed to a functional shape which takes the general form of a cup in which at least a portion of the bottom is substantially flat.

7. The device of claim 6 in which the rim of the functional shape includes an outwardly extending flange.

8. The device of claim 6 further comprising a cylindrical holder.

9. A device for separating plasma from blood comprising a synthetic polymeric fibrous structure having a CWST in excess of 65 dynes/cm, the structure having a first region for receiving a blood sample and a second region for accumulating plasma, the device further comprising a porous guard layer cooperatively arranged with the second region of the structure to allow passage of plasma and prevent passage of red blood cells.

10. The device of claim 9 in which the porous guard layer is secured to the second region of the fibrous structure.

11. The device of claim 10 in which the fibers in the fibrous structure have been formed to a functional shape.

12. The device of claim 11 in which the functional shape takes the general form of a cup in which at least a portion of the bottom is substantially flat.

13. The device of claim 12 in which the rim of the functional shape includes an outwardly extending flange.

14. The device of claim 9 further comprising a holder.

15. The device of claim 14 in which the holder is cylindrical.

16. The device of claim 15 in which the fibers in the fibrous structure have been formed in a cup shape, wherein at least a portion of the bottom of the cup shape projects beyond one end of the cylindrical holder.

17. The device of claim 14 in which the fibrous structure and porous guard layer are centrally located within and affixed to the inner wall of the holder.

18. The device of claim 17 further comprising means for the application of vacuum to the first region, thereby inducing flow from the second region to the first region.

19. The device of claim 17 further comprising means for positioning an absorbent pad in cooperative arrangement with the first region.

20. The device of claim 9, in which the guard layer is a microporous membrane.

21. The device of claim 20 in which the membrane is a hydrophilic nylon 66 membrane.

22. The device of claim 20 in which the membrane is a polyamide selected from the group consisting of nylon 6, nylon 66, and nylon 610.

23. The device of claim 20 in which the membrane is a fluorocarbon resin membrane the surfaces of which have been rendered hydrophilic.

24. A device for separating plasma from blood comprising a synthetic polymeric fibrous structure having a CWST in excess of 65 dynes/cm, the structure having a first region for receiving a blood sample and a second region for accumulating plasma, in which the first region is a recess in the fibrous structure, wherein the structure has a functional shape generally resembling a cup with a substantially flat bottom.

25. The device of claim 24 wherein the voids volume of the fibrous structure is such that the volume of the received blood sample is sufficient to substantially fill the voids volume.

26. The device of claim 24 further comprising a holder to facilitate manipulation.

27. The device of claim 24 further comprising a holder for the fibrous structure at least a portion of which is cylindrical.

28. The device of claim 27 in which the substantially flat bottom portion of the structure projects from one end of the holder.

29. A device for separating plasma from blood comprising a synthetic polymeric fibrous structure having a CWST in excess of 65 dynes/cm, the structure having a first region for receiving a blood sample and a second region for accumulating plasma, the device further comprising a structure with a higher capillary attraction cooperatively arranged with the second region, wherein the structure with a higher capillary attraction is a microporous membrane.

30. The device of claim 29 wherein the membrane comprises a polyamide.

31. The device of claim 30 wherein the polyamide comprises nylon 66.

32. A device for separating plasma from blood comprising a synthetic polymeric fibrous structure having a CWST in excess of 65 dynes/cm, and a $V_f$ of greater than 0.2 cc/cc, the structure having a first region for receiving a blood sample and a second region for accumulating plasma and a porous guard layer cooperatively arranged with the second region to allow passage of plasma and prevent passage of red blood cells.

33. The device of claim 32 in which $V_f$ is greater than 0.24 cc/cc.

34. The device of claim 32 in which the average fiber diameter of the fibers in the fibrous structure is less than about 3 micrometers.

35. The device of claim 32 in which the fibrous structure is comprised of multiple layers of a fibrous web.

36. The device of claim 32 in which the fibers in the fibrous structure comprise polybutylene terephthalate.

37. The device of claim 36 in which the polybutylene terephthalate fibers have been modified to present hydroxyl groups and the structure has a CWST in excess of 95 dynes/cm.

38. The device of claim 37 in which the fibers have been modified with HEMA using radiation and the structure has a CWST in excess of 110 dynes/cm.

39. A device for separating plasma from blood comprising a fibrous structure having a CWST in excess of 65 dynes/cm, the structure having a first region for receiving a blood sample, a second region for accumulating plasma, and a porous guard layer cooperatively arranged with the second region to allow passage of plasma and prevent passage of red blood cells.

40. A self-contained device for separating plasma from blood and carrying out a diagnostic test comprising a fibrous structure having a CWST in excess of 65 dynes/cm, the structure having a first region for receiving a blood sample, a second region for accumulating plasma, and a porous guard layer cooperatively arranged with the second region to allow passage of plasma and prevent passage of red blood cells, the porous guard layer also serving as a diagnostic medium.

41. The device of claim 40 wherein said porous guard layer is a hydrophilic, microporous nylon membrane.

42. The device of claim 40 contained within a holder.

43. The self-contained device of claim 40 in which the porous guard layer has a first surface in contact with the fibrous structure and a second surface including a region for carrying out a diagnostic test.

44. The device of claim 43 comprising multiple fibrous structures in an array, each of the fibrous structures having a porous guard layer in contact with its respective second region.

45. The device of claim 43 comprising multiple discrete fibrous structures each secured in a holder in array form and each of the fibrous structures having a discrete porous guard layer secured to the second region of the respective fibrous structure.

46. The device of claim 45 wherein the holder is a microtiter plate.

47. A method for conducting a diagnostic test using a device for separating plasma from blood comprising a synthetic polymeric fibrous structure having a CWST in excess of 65 dynes/cm, the structure having a first region for receiving a blood sample and a second region for accumulating plasma, the device further comprising (i) a holder and (ii) a porous guard layer cooperatively arranged with the second region of the structure to allow passage of plasma and prevent passage of red blood cells; the method comprising adding blood at the first region in a first step, followed by a second step in which one or more liquid reagents pass through the porous guard layer, thence through the second region, and thence through the first region.

48. The method of claim 47 in which following the second step one or more aqueous based wash fluids, and then one or more additional liquid reagents are passed through the porous guard layer, thence through the second region, and thence through the first region.

49. The method of claim 47 wherein the device for separating plasma from blood further comprises means for the application of vacuum to the first region, thereby inducing flow from the second region to the first region.

50. The method of claim 47 wherein the device for separating plasma from blood further comprises means for positioning an absorbent pad in cooperative arrangement with the first region.

51. A method for separating plasma from blood comprising:
a) contacting a plasma containing blood sample with a first region of a fibrous structure, wherein the structure has a CWST in excess of about 65 dynes/cm and includes the first region, a second region for accumulating plasma, and wherein a porous guard layer is cooperatively arranged with the second region to allow passage of plasma and prevent passage of red blood cells; and
b) accumulating plasma in the second region of the fibrous structure, thereby separating the plasma from the blood sample.

* * * * *